United States Patent
Lee et al.

(10) Patent No.: US 11,406,588 B2
(45) Date of Patent: Aug. 9, 2022

(54) **METHOD FOR ELIMINATING ODORS COMPRISING A DEODORANT COMPOSITION CONTAINING *OPUNTIA FICUS* EXTRACT OR PERSIMMON JUICE**

(71) Applicant: THE WELLNESS LIFE INSTITUTE CO., LTD., Jeju-si (KR)

(72) Inventors: Hyun Joo Lee, Jeju-si (KR); Ha Young Choi, Jeju-si (KR); Na Young Choi, Jeju-si (KR); Ha Young Song, Seoul (KR)

(73) Assignee: THE WELLNESS LIFE INSTITUTE CO., LTD., Jeju-si (KR)

( * ) Notice: Subject to any disclaimer, the term of this patent is extended or adjusted under 35 U.S.C. 154(b) by 0 days.

(21) Appl. No.: 17/097,769

(22) Filed: Nov. 13, 2020

(65) Prior Publication Data

US 2021/0330577 A1 Oct. 28, 2021

(30) Foreign Application Priority Data

Apr. 28, 2020 (KR) ........................ 10-2020-0051400

(51) Int. Cl.
*A61K 8/9789* (2017.01)
*A61Q 11/00* (2006.01)

(52) U.S. Cl.
CPC ............ *A61K 8/9789* (2017.08); *A61Q 11/00* (2013.01)

(58) Field of Classification Search
CPC ............... A61K 36/33; A61P 1/04; A61P 3/00
USPC .............................. 514/457; 424/47, 65, 767
IPC ....................................................... A61Q 15/00
See application file for complete search history.

(56) References Cited

U.S. PATENT DOCUMENTS

| | | | | |
|---|---|---|---|---|
| 6,139,842 A | * | 10/2000 | Matsuda | A61K 8/732 424/771 |
| 2007/0003492 A1 | * | 1/2007 | Kitahata | A61Q 15/00 424/49 |
| 2010/0323045 A1 | * | 12/2010 | Pischel | A61P 1/04 424/767 |

* cited by examiner

*Primary Examiner* — Walter E Webb
(74) *Attorney, Agent, or Firm* — Sughrue Mion, PLLC

(57) ABSTRACT

Disclosed is a method for eliminating odors including administering a deodorant composition containing an *Opuntia ficus* (prickly pear) extract or a fraction thereof as an active ingredient. The deodorant composition, which further contains a persimmon extract or a fraction thereof, a persimmon juice, or a green tea extract or a fraction thereof, is useful as a deodorizer for removing or reducing ammonia and trimethylamine.

5 Claims, No Drawings

METHOD FOR ELIMINATING ODORS COMPRISING A DEODORANT COMPOSITION CONTAINING *OPUNTIA FICUS* EXTRACT OR PERSIMMON JUICE

CROSS REFERENCE TO RELATED APPLICATIONS

The instant application claims priority based on Korean Patent Application No. 10-2020-0051400 filed Apr. 28, 2020, of which the entire content is incorporated herein by reference.

BACKGROUND OF THE INVENTION

Field of the Invention

An aspect of the invention, the present invention relates to a method for eliminating odors comprising administering a deodorant composition containing an *Opuntia ficus* (prickly pear) extract, a persimmon extract, persimmon juice, a *Cryptomeria japonica* (cedar) extract or a green tea extract.

Description of the Related Art

In addition to noise, vibration and dust, which cause discomfort in everyday life, odors are regulated as pollution and regulations based on related laws are becoming more stringent.

Typically, odors are classified into acidic odors such as hydrogen sulfide, mercaptan, methyl sulfide and methyl disulfide, basic odors such as ammonia, trimethylamine, and skatole, and neutral odors such as acetaldehyde or styrene. An odor is defined as a smell that causes discomfort and disgust by stimulating the human sense of smell using hydrogen sulfide, mercaptans, amines and other irritating gaseous substances. These odors stimulate the human sense of smell and harm the pleasant emotional life and even the health of humans. Life-related odors include a variety of smells such as the smell of food waste, the smell of the refrigerator, the smell of the shoe rack, the smell of the toilet, the smell of the damp laundry in the rainy season and the musty smell at a high humidity. In particular, ammonia is one of the main components of odors in everyday life, and is mainly generated from pet feces, food waste and toilets. In order to suppress or remove odors such as odors derived from ammonia, perfumes or fragrances are sprayed, or various deodorants are used. However, it is common for most chemical perfumes and fragrances to simply cover the odor with a stronger scent rather than remove the odor. Accordingly, there is a side effect of causing an unexpected unpleasant smell or headache due to the mixture of odor and chemical perfumes or fragrances.

In addition, recently, problems related to a sick house syndrome have arisen due to the use of materials containing harmful chemicals such as low-cost formaldehyde (HCHO) and volatile organic compounds (VOCs) in wallpaper and floor materials used in apartments or detached houses.

Accordingly, there is a need to develop an environmentally friendly deodorant that can efficiently eliminate odors from such causes (sources).

REFERENCE

Patent Document (Patent Document 1) Korean Patent Laid-Open No. 10-1997-0061276

SUMMARY OF THE INVENTION

Accordingly, it is one object of the present invention to provide a deodorant composition containing an *Opuntia ficus* extract or a fraction thereof as an active ingredient.

It is another object of the present invention to provide a deodorant food composition containing the deodorant composition.

It is another object of the present invention to provide a deodorant cosmetic composition containing the deodorant composition.

It is another object of the present invention to provide an oral composition for eliminating bad breath (halitosis) containing the deodorant composition.

It is another object of the present invention to provide a method for eliminating odors including performing treatment with the deodorant composition.

It is another object of the present invention to provide a method for eliminating odors from a subject comprising administering a composition comprising an *Opuntia ficus* (prickly pear) extract or a fraction thereof as an active ingredient to the subject.

It is another object of the present invention to provide a method for reducing ammonia and/or trimethylamine for reducing body odor or malodor of oral cavity, comprising topically administering a composition comprising an *Opuntia ficus* (prickly pear) extract or a fraction thereof as an active ingredient to body or oral cavity of the subject.

In accordance with the present invention, the above and other objects can be accomplished by the provision of a deodorant composition containing an *Opuntia ficus* extract or a fraction thereof as an active ingredient.

DETAILED DESCRIPTION OF THE INVENTION

In the present invention, the term "prickly pear" is interchangeable with "opuntia", and the scientific name of the plant denoted thereby is *Opuntia ficus*, which is cultivated in large amounts as a special crop on Jeju Island. Prickly pear is used to treat burns, swelling, indigestion, boils, bronchial asthma and the like, and the ethanol extract of fruits and stems has effects such as the effect of protecting gastric mucosa based on analgesic and anti-inflammatory activities, the effect of controlling blood sugars, and the effect of enhancing immunity.

As herein used, the term "extract" encompasses an extract liquid itself and an extract substance in the form of any formulation that can be prepared using the extract liquid, such as an extract liquid obtained through an extraction process, a dilution or concentrate of the extract liquid, a dried product obtained by drying the extract liquid, a partially or wholly purified product of the extract liquid, or a mixture thereof.

In the present invention, the drying of prickly pear may be performed by a known method within a range within which useful components in prickly pear or fruit thereof are not destroyed. For example, the drying may be natural shade drying. Further, the crushing or pulverization may be performed to realize powderization by crushing or pulverizing to an extent such that the useful components of prickly pear can be sufficiently extracted in the subsequent extraction process. The drying and crushing or pulverizing process may be performed in the reverse order, or may be repeatedly performed as necessary.

In the extraction of the present invention, the method of extracting is not particularly limited and the extraction may be carried out according to a method commonly used in the art. Non-limiting examples of the extraction method include hot water extraction, ultrasonic extraction, filtration, reflux extraction, and the like. This extraction method may be performed alone or in combinations of two or more methods.

The prickly pear extract may be an extract of prickly pear fruit, and may be obtained by extracting the prickly pear or fruit thereof using water, an organic solvent, or a mixed solvent thereof. Specifically, the prickly pear extract may be obtained from the dried fruit or powder thereof using, as an extraction solvent, an alcohol having 1 ($C_1$) to 4 ($C_4$) carbon atoms, such as water, methanol, ethanol, propanol, isopropanol, butanol, or a mixed solvent thereof, and more specifically, the alcohol may be ethanol.

In one embodiment of the present invention, an ethanol extract of the prickly pear fruit cultivated on Jeju Island is prepared by mixing the fruits of the lyophilized prickly pear with an about 70% ethanol extract.

As used herein, the term "fraction" means a product obtained by fractionation for separating a specific component or a specific group from a mixture containing various components.

In the present invention, the fractionation method for obtaining the fraction is not particularly limited, and the fractionation may be performed according to a method commonly used in the art. A non-limiting example of the fractionation method is a method of obtaining a fraction from a prickly pear extract by treating the prickly pear extract with a predetermined solvent.

In the present invention, the type of solvent used to obtain the fraction is not particularly limited, and any solvent known in the art may be used. Non-limiting examples of the fractionation solvent include water, alcohol having 1 to 4 carbon atoms, hexane, ethyl acetate, chloroform, dichloromethane, or mixed solvents thereof.

As herein used, the term "deodorization" means removal of an odor or bad smell. Deodorization in the present invention specifically refers to deodorization of ammonia or trimethylamine to reduce the concentration of ammonia or trimethylamine.

In the present invention, the deodorant composition may further include at least one selected from the group consisting of a persimmon extract or fraction thereof, a persimmon juice, and a green tea extract or a fraction thereof.

In the present invention, the definitions of the terms of "extract" and "fraction" are as given above.

The persimmon may be derived from "*Diospyros kaki*", the Jeju persimmon tree, which grows naturally on Jeju Island. The *Diospyros kaki*, which is native to Jeju Island, has been used for dyeing traditional Jeju cloth called "Galot", and the tannin content thereof is much higher than that of ordinary persimmons, and the size of mature fruits thereof is also smaller than that of ordinary persimmons. The persimmon may be green (unripe) persimmon, which is an immature fruit of the persimmon tree.

The persimmon juice is a juice obtained from unripe persimmons (green persimmons), which is also referred to as a persimmon liquid, and has mainly been used as a dye for dyeing Galot.

Cedar has the scientific name of *Cryptomeria japonica*, grows to about 40 m in height and about 1 to 2 m in diameter, and has leaves having 3 to 4 hairs clustered to form a sharp needle-shaped end. In Korea, it is widely distributed on Jeju Island and southern regions, and is mainly used in windbreaks, as construction timber, and in the landscaping industry. The cedar used herein may be an extract of cedar sawdust or a fraction thereof, prepared by drying the heartwood, sapwood or stems of cedar from Jeju.

Green tea has the scientific name *Camellia sinensis*, and may be an extract of leaves of a green tea tree obtained from Jeju or a fraction thereof.

In one embodiment of the present invention, it was found that the ethanol extract of the fruit of prickly pear derived from Jeju exhibits a deodorizing effect by reducing the concentration of ammonia and trimethylamine.

In addition, in one embodiment of the present invention, the ethanol extract of unripe persimmon from Jeju, the juice (persimmon liquid) of unripe persimmon from Jeju, and the ethanol extract of green tea leaves from Jeju also exhibit a deodorizing effect by reducing the concentration of ammonia and trimethylamine, similar to the ethanol extract of the fruit of prickly pear.

In addition, it was found that a mixed extract, prepared by mixing the ethanol extract of unripe persimmon from Jeju, the ethanol extract of prickly pear from Jeju, the ethanol extract of green tea leaves from Jeju, and the ethanol extract of cedar from Jeju, exhibited a deodorizing effect against ammonia and trimethylamine.

In another aspect, the present invention provides a deodorant cosmetic composition for deodorization containing the deodorant composition.

The cosmetic composition of the present invention may contain a compound or a natural extract known to have a deodorizing effect so as to increase or reinforce the deodorizing effect, in addition to the prickly pear extract or fraction thereof, the persimmon extract or fraction thereof, the persimmon juice and the green tea extract or fraction thereof, which are active ingredients of the deodorizing composition.

Meanwhile, in the cosmetic composition of the present invention, the active ingredient may be present in a predetermined amount (effective amount) depending on the application, formulation, purpose of mixing, etc., so long as it can exhibit a deodorizing effect, and a typical effective amount is within the range of 0.001% by weight to 99.99% by weight based on the total weight of the composition. Here, "effective amount" refers to an amount of the active ingredient that can induce the deodorizing effect. Such an effective amount may be determined empirically within the range of ordinary skill of those skilled in the art.

The cosmetic composition of the present invention may be prepared in various forms. For example, the cosmetic composition of the present invention may be prepared in any formulation commonly prepared in the art, such as a solution, suspension, emulsion, paste, gel, cream, lotion, powder, soap, cleanser, oil, powder foundation, emulsion foundation, wax foundation or spray, but is not limited thereto. In addition, specifically, the cosmetic composition of the present invention may have a formulation selected from the group consisting of skin lotion, skin softener, skin toner, astringent, lotion, milk lotion, moisture lotion, nutrition lotion, massage cream, nutrition cream, moisture cream, hand cream, essence, nutrition essence, pack, soap, shampoo, cleansing foam, cleansing lotion, cleansing cream, body lotion, body cleanser, emulsion, lipstick, makeup base, foundation, press face powder, loose face powder, and deodorant stick, but is not limited thereto.

The cosmetic composition of the present invention may include a carrier that is acceptable in a cosmetic preparation, in addition to the active ingredient. Herein, "acceptable carrier in a cosmetic preparation" refers to a compound or composition that is already known and used and may be contained in a cosmetic preparation, or a compound or composition that is to be developed in the future, that exhibits no toxicity, instability or irritation beyond what the human body can tolerate when in contact with the skin. The carrier may be present in the cosmetic composition of the present invention in an amount of about 1% by weight to about 99.99% by weight, preferably about 5% by weight to about 99% by weight, based on the total weight of the cosmetic composition. However, this proportion varies depending on the formulation of the cosmetic of the present invention to be prepared, the specific area (face or hand), to which the cosmetic is applied, or the preferred amount of the applied cosmetic, and should not be construed as limiting the scope of the present invention in any aspect.

Meanwhile, examples of the carrier include alcohols, oils, surfactants, fatty acids, silicone oils, wetting agents, moisturizing agents, viscosity modifiers, emulsions, stabilizers, UV blockers, coloring agents, fragrances, and the like. The compounds and/or compositions that can be used as alcohols, oils, surfactants, fatty acids, silicone oils, wetting agents, moisturizing agents, viscosity modifiers, emulsions, stabilizers, UV blockers, coloring agents, and fragrances in the carrier are already known in the art. Therefore, those skilled in the art can select and use an appropriate corresponding substance and/or composition.

In an aspect of the present invention, an oral care composition is provided. The oral care composition may have a form of a paste, gel, lozenge, gum, or liquid formulation. In another aspect, the oral care composition may have a form of a film of any desired shape or structure, including multiple small strips, or one continuous strip.

In another aspect, the present invention provides a food composition for deodorization containing the deodorant composition.

The food composition of the present invention may have a formulation such as a pill, powder, granule, infusion, tablet, capsule, chewing gum or jelly, lozenge, or liquid, and there is no particular limitation on the type of the food composition of the present invention. Examples of the food to which the substance can be added include meat, sausage, bread, chocolate, candy, snacks, confectionery, pizza, ramen, other noodles, chewing gum or jelly, dairy products including ice cream, various soups, beverages, tea, drinks, alcoholic beverages, and dietary supplements.

In addition to the prickly pear extract or fraction thereof, persimmon extract or fraction thereof, persimmon juice and green tea extract or fraction thereof, the food composition may further contain another component, and the kind of another component is not particularly limited. For example, the food composition may contain an additional component selected from various herbal extracts, cytologically acceptable food supplementary additives or natural carbohydrates, like ordinary foods, but is not limited thereto.

In the present invention, the term "food supplementary additive" means an auxiliary component that can be added to food and is a compound that is added to prepare foods according to respective formulations, and can be appropriately selected and used by those skilled in the art. Examples of the food supplementary additive include various nutrients, vitamins, minerals (electrolytes), flavoring agents such as synthetic flavoring agents and natural flavoring agents, coloring agents and fillers, pectic acid and salts thereof, alginic acid and salts thereof, organic acids, protective colloid thickeners, pH regulators, stabilizers, preservatives, glycerin, alcohol, carbonation agents used in carbonated beverages and the like, but the type of the food supplementary additive of the present invention is not limited by the above examples.

Examples of the natural carbohydrates include monosaccharides such as glucose and fructose, disaccharides such as maltose and sucrose, polysaccharides such as dextrin and cyclodextrin, and sugar alcohols such as xylitol, sorbitol and erythritol. As flavoring agents other than those described above, natural flavoring agents (thaumatin, etc.), stevia extracts (rebaudioside A, glycyrrhizin, etc.) and synthetic flavoring agents (saccharin, aspartame, etc.) can be used advantageously.

The food composition of the present invention may contain a health functional food. As used herein, the term "health functional food" refers to a food prepared and processed in the form of a tablet, capsule, powder, granule, liquid or pill using raw materials or ingredients having beneficial functions for the human body. Here, the term "functionality" refers to an obtained effect that is useful for health purposes, such as control of nutrients or physiological effects with regard to the construction and function of the human body. The health functional food of the present invention can be prepared by a method commonly used in the art, and the preparation may be carried out by adding raw materials and ingredients commonly added in the art. In addition, unlike general drugs, the health functional food contains a food as a raw material and thus has the advantages of not causing side effects that may occur when administering drugs for a long time and of exhibiting excellent portability.

The mixing amount of the active ingredient may be appropriately determined according to the purpose of use (prevention, health or therapeutic treatment). In general, when preparing a food, the active ingredient of the present invention may be added in an amount of 1 to 50% by weight, preferably 5 to 10% by weight, of the raw material composition, but is not limited thereto. However, in the case of long-term intake for the purpose of health and hygiene or for health maintenance purposes, the amount that is used may even be below the above range.

The health functional food is ingested in the form of an inner beauty food and thus has the advantage of having a further improved deodorization effect. The term "inner beauty food", which is also called an "eaten cosmetic" or "beauty food", is referred to a food that makes the skin constitution healthy by absorbing various ingredients beneficial for the skin into the body. Just like choosing cosmetics that fit the skin type, an inner beauty food that suits each individual can be chosen and consumed in consideration of skin condition and lifestyle. More specifically, the use of a cosmetic containing the cosmetic composition in combination with an inner beauty food containing the prickly pear extract or fraction thereof exhibits a significantly higher deodorizing effect and is thus more effective than a single use of the cosmetic.

In another aspect, the present invention provides an oral composition for eliminating bad breath containing the deodorant composition.

In addition, the present invention can be applied as an oral composition. Bad breath occurs as follows. Many microorganisms that degrade proteins and amino acids live in the oral cavity. Amino acids are produced when proteins and food debris in saliva are decomposed by microorganisms in the oral cavity, and the amino acids are decomposed by acid demineralization enzymes or amino enzymes to produce substances that cause bad breath. In addition, bad breath is primarily caused by bacterial spoilage caused by bacteria and by sulfides contained in consumed garlic or red pepper. The main components that cause bad breath are volatile sulfide compounds (hereinafter abbreviated as "VSC"), and these volatile sulfides include hydrogen sulfide (H₂S), methyl mercaptan (CH₃SH), dimethyl mercaptan ((CH₃)₂S), and the like. In particular, methyl mercaptan is known to be the main component of the disgusting odor in bad breath. In addition, as the freshness of fish decreases, fish produces trimethylamine [(CH₃)₃N] or δ-aminovaleric acid, which causes the odor of the fish, and of these volatile amine compounds, trimethylamine, is a particularly important bad breath component. The consumption of fish may cause bad breath due to trimethylamine, etc. in the oral cavity. In addition, other bad-breath-causing substances include aldehydes, fatty acids, ammonia, pyridine and the like.

The composition of the present invention has an excellent effect of deodorizing substances that cause bad breath such as ammonia and trimethylamine, which cause odors in the oral cavity and thus can be applied to an oral composition for removing or alleviating bad breath.

In another aspect, the present invention provides a method for eliminating odors including performing treatment with the deodorant composition.

In the present invention, when treatment with the deodorant composition is performed, the concentration of ammonia and trimethylamine can be reduced, so deodorization is possible. Therefore, air purification is possible by removing odors common in various indoor industrial and home environments such as factory wastewater, groundwater, garbage disposal plants, refrigerators, shoe racks and toilets.

In another aspect, the present invention provides a method for eliminating odors from a subject comprising administering a composition comprising an *Opuntia ficus* (prickly pear) extract or a fraction thereof as an active ingredient to the subject.

The terms "*Opuntia ficus* (prickly pear)", "extract", "fraction" and "composition" as used herein are the same as defined above.

The term "subject" as used herein refers to all animals, including humans who have generate odors. The subject includes mammals including cows, pigs, sheep, chickens, dogs, humans, and the like, and includes, but is not limited to, the subject in which the odor is eliminated via administration of the composition of the present invention.

In the present invention, the odor means malodor of oral cavity or halitosis. The composition of the present invention may be used in the form of an oral care composition as an example. The oral care composition may have a form of a paste, gel, lozenge, gum, or liquid formulation. In another aspect, the oral care composition may have a form of a film of any desired shape or structure, including multiple small strips, or one continuous strip.

The composition further comprises one or more selected from the group consisting of a persimmon extract, a fraction of persimmon extract, a persimmon juice, a green tea extract, and a fraction of the green tea extract.

The *Opuntia ficus* (prickly pear) extract is obtained using, as an extraction solvent, water, an alcohol having 1 to 4 carbon atoms, or a mixed solvent thereof.

The persimmon is green (unripe) persimmon, which is an immature fruit from a persimmon tree.

The administering the composition reduces a concentration of ammonia or trimethylamine generated from the subject.

The composition of the present invention has an excellent effect of deodorizing substances that cause bad breath such as ammonia and trimethylamine, which cause odors in the oral cavity and thus can be applied to an oral cavity for removing or alleviating bad breath.

Therefore, the malodor of oral cavity or halitosis can be removed from oral cavity of the subject by administering the composition.

In another aspect, the present invention provides a method for reducing ammonia and/or trimethylamine for reducing body odor or malodor of oral cavity, comprising topically administering a composition comprising an *Opuntia ficus* (prickly pear) extract or a fraction thereof as an active ingredient to body or oral cavity of the subject.

The present invention specifically reduces the concentration of ammonia or trimethylamine by deodorizing ammonia or trimethylamine generated in the body and thus reduces an odor or bad smell from body.

The composition of the present invention may be used in the form of a cosmetic composition, a food composition, or an oral care composition for application to the body as examples.

The composition of the present invention can be applied to the skin as a cosmetic composition and remove odor from the body.

The terms "*Opuntia ficus* (prickly pear)", "extract", "fraction", "subject", "cosmetic composition", "food composition" and "composition" as used herein are the same as defined above.

In addition, the composition of the present invention has an excellent effect of deodorizing substances that cause bad breath such as ammonia and trimethylamine, which cause odors in the oral cavity.

The composition of the present invention may be used in the form of an oral care composition as an example. The oral care composition may have a form of a paste, gel, lozenge, gum, or liquid formulation. In another aspect, the oral care composition may have a form of a film of any desired shape or structure, including multiple small strips, or one continuous strip.

Therefore, the composition of the present invention can be applied to body or oral cavity for reducing ammonia and/or trimethylamine generated in the subject.

The composition further comprises one or more selected from the group consisting of a persimmon extract, a fraction of persimmon extract, a persimmon juice, a green tea extract, and a fraction of the green tea extract.

The *Opuntia ficus* (prickly pear) extract is obtained using, as an extraction solvent, water, an alcohol having 1 to 4 carbon atoms, or a mixed solvent thereof.

The persimmon is green (unripe) persimmon, which is an immature fruit from a persimmon tree.

Hereinafter, the present invention will be described in more detail with reference to exemplary embodiments such that the present invention can be easily implemented by those skilled in the art. However, the present invention can be implemented in various forms, and these examples should not be construed as limiting the scope of the present invention.

Example 1. Preparation of Ethanol Extract of Unripe Persimmon from Jeju 300 g of dried unripe persimmon (*Diospyros kaki*) from Jeju was mixed with a 70% ethanol (EtOH) solution and extracted under optimal conditions (70° C., 20 hours) in a shaking incubator. After extraction, the 70% ethanol extract was filtered, and the filtrate was collected.

Example 2. Preparation of Juice of Unripe Persimmon (Persimmon Liquid) from Jeju The dried unripe persimmon (*Diospyros kaki*) from Jeju was squeezed using a juicer to obtain an unripe persimmon juice (persimmon liquid).

Example 3. Preparation of Ethanol Extract of Prickly Pear from Jeju 300 g of lyophilized fruit of prickly pear (*Opuntia ficus*) from Jeju was mixed with a 70% ethanol (EtOH) solution and extracted under optimal conditions (70° C., 20 hours) in a shaking incubator. After extraction, the 70% ethanol extract was filtered, and the filtrate was collected.

Example 4. Preparation of Ethanol Extract from Leaves of Green Tea from Jeju 300 g of dried leaves of green tea (*Camellia sinensis*) from Jeju were mixed with a 70% ethanol (EtOH) solution and extracted under optimal conditions (70° C., 20 hours) in a shaking incubator. After extraction, the 70% ethanol extract was filtered, and the filtrate was collected.

Comparative Example 1. Preparation of Ethanol Extract of Cedar from Jeju 300 g of sawdust of cedar (*Cryptomeria japonica*) from Jeju was mixed with a 70% ethanol (EtOH) solution and extracted under optimal conditions (70° C., 20 hours) in a shaking incubator. After extraction, the 70% ethanol extract was filtered, and the filtrate was collected.

Example 5. Preparation of Mixed Extract

The ethanol extract of unripe persimmon from Jeju of Example 1, the ethanol extract of *Opuntia ficus* from Jeju of Example 3, the ethanol extract of green tea (*Camellia sinensis*) leaves from Jeju of Example 4, and the ethanol extract of cedar (*Cryptomeria japonica*) from Jeju of Comparative Example 1 were mixed at a volume ratio (v/v) of 1:1:1:1 to prepare a mixed extract.

Experimental Example 1. Evaluation of Deodorizing Effect

The deodorization effects against ammonia, trimethylamine, hydrogen sulfide and methyl mercaptan were evaluated based on the EL608:2017 test method using a 1 L test container, and 20 mL of each of the ethanol extract of unripe persimmon from Jeju of Example 1, juice of unripe persimmon (persimmon liquid) from Jeju of Example 2, the ethanol extract of *Opuntia ficus* from Jeju of Example 3, the ethanol extract of green tea (*Camellia sinensis*) leaves from Jeju of Example 4, the mixed extract of Example 5, and the ethanol extract of cedar (*Cryptomeria japonica*) from Jeju of Comparative Example 1.

As shown in Table 1, the result showed that the ethanol extract of unripe persimmon from Jeju of Example 1, juice of unripe persimmon (persimmon liquid) from Jeju of Example 2, the ethanol extract of *Opuntia ficus* from Jeju of Example 3, the ethanol extract of green tea (*Camellia sinensis*) leaves from Jeju of Example 4, and the mixed extract of Example 5 exhibited an excellent deodorizing effect against ammonia and trimethylamine, but had no deodorizing effect against hydrogen sulfide or methyl mercaptan. In particular, the juice of unripe persimmon from Jeju showed the best deodorizing effect against ammonia and trimethylamine. However, the ethanol extract of cedar from Jeju of Comparative Example 1 had no deodorizing effect against ammonia, trimethylamine, hydrogen sulfide and methyl mercaptan.

In addition, because the mixed extract of Example 5 is prepared in the same volume of 20 mL by mixing the ethanol extract of unripe persimmon from Jeju of Example 1, the ethanol extract of *Opuntia ficus* from Jeju of Example 3, the ethanol extract of green tea (*Camellia sinensis*) leaves from Jeju of Example 4, and the ethanol extract of cedar (*Cryptomeria japonica*) from Jeju of Comparative Example 1 at a volume ratio (v/v) of 1:1:1:1, the content of the extracts of Examples 1, 3, and 4 was reduced to 15 ml due to the addition of the ethanol extract of cedar from Jeju according to Comparative Example 1 and thus the deodorizing effect was relatively low.

TABLE 1

| NO | Sample | Deodorization test: Concentration decrease (%) | | | |
| --- | --- | --- | --- | --- | --- |
| | | Ammonia | Trimethylamine | Hydrogen sulfide | Methyl mercaptan |
| Example 1 | Ethanol extract of unripe persimmon from Jeju | 60.0 | 62.5 | 0.0 | 0.0 |
| Example 2 | Juice of unripe persimmon (persimmon liquid) from Jeju | 90.0 | 87.5 | 0.0 | 0.0 |
| Example 3 | Ethanol extract of *Opuntia ficus* fruits from Jeju | 65.0 | 62.5 | 0.0 | 0.0 |
| Example 4 | Ethanol extract of green tea leaves from Jeju | 70.0 | 75.0 | 0.0 | 0.0 |
| Example 5 | Mixed extract- Example 1:Example 3:Example 4:Comparative Example 1 (1:1:1:1) | 70.0 | 62.5 | 0.0 | 0.0 |
| Comparative Example 1 | Ethanol extract of sawdust of cedar from Jeju | 0.0 | 0.0 | 0.0 | 0.0 |

As apparent from the foregoing, the present invention is directed to a deodorant composition containing an *Opuntia ficus* (prickly pear) extract or a fraction thereof as an active ingredient. The deodorant composition, which further contains a persimmon extract or a fraction thereof, a persimmon juice, or a green tea extract or fraction thereof, can be useful as a deodorizer for ammonia and trimethylamine.

Although the preferred embodiments of the present invention have been disclosed, those skilled in the art will appreciate that various modifications, additions and substitutions are possible, without departing from the scope and spirit of the invention as disclosed in the accompanying claims.

What is claimed is:

1. A method for eliminating odor from a subject comprising administering a composition comprising an ethanol extract of *Opuntia ficus* (prickly pear) fruit, an ethanol extract of green (unripe) persimmon, and an ethanol extract of green tea leaf, as an active ingredient to the subject, wherein the administering the composition reduces a concentration of ammonia or trimethylamine generated from the subject.

2. The method of claim 1, wherein the odor is malodor of oral cavity or halitosis.

3. The method of claim 1, wherein the composition further comprises a green (unripe) persimmon juice.

4. A method for reducing ammonia and/or trimethylamine for reducing body odor or malodor of oral cavity, comprising topically administering a composition comprising an ethanol extract of *Opuntia ficus* (prickly pear) fruit, an ethanol extract of green (unripe) persimmon, and an ethanol extract of green tea leaf, as an active ingredient to body or oral cavity of the subject.

5. The method of claim 4, wherein the composition further comprises a green (unripe) persimmon juice.

* * * * *